US012357594B1

(12) United States Patent
Balbinot et al.

(10) Patent No.: US 12,357,594 B1
(45) Date of Patent: Jul. 15, 2025

(54) ANTIMICROBIAL SOLUTION FOR PRE-OPERATIVE PREPARATION (71) Applicant: Sage Products, LLC, Cary, IL (US)

(72) Inventors: Jodi M. Balbinot, Cary, IL (US); Jennifer M. Allen, Cary, IL (US)

(73) Assignee: Sage Products, LLC, Cary, IL (US)

( * ) Notice: Subject to any disclaimer, the term of this patent is extended or adjusted under 35 U.S.C. 154(b) by 10 days.

(21) Appl. No.: 17/853,389

(22) Filed: Jun. 29, 2022

Related U.S. Application Data (60) Provisional application No. 63/217,023, filed on Jun. 30, 2021.

(51) Int. Cl.
*A61K 31/155* (2006.01)
*A61K 9/00* (2006.01)
*A61K 9/08* (2006.01)
*A61K 31/045* (2006.01)
*A61K 47/26* (2006.01)
*A61P 31/02* (2006.01)

(52) U.S. Cl.
CPC .......... *A61K 31/155* (2013.01); *A61K 9/0014* (2013.01); *A61K 9/08* (2013.01); *A61K 31/045* (2013.01); *A61K 47/26* (2013.01); *A61P 31/02* (2018.01)

(58) Field of Classification Search
CPC ...... A61K 31/155; A61K 9/0014; A61K 9/08; A61K 31/045; A61K 47/26; A61P 31/02
See application file for complete search history.

(56) References Cited

U.S. PATENT DOCUMENTS

| | | | |
|---|---|---|---|
| 7,582,681 B2 | 9/2009 | Schmaus et al. | |
| 7,683,018 B2 | 3/2010 | Koivisto et al. | |
| 8,173,183 B2 | 5/2012 | Hergert | |
| 9,074,434 B2 | 7/2015 | Mensa-Wilmot | |
| 9,598,471 B2 | 3/2017 | Renye et al. | |
| 9,987,232 B2 | 6/2018 | New | |
| 10,201,581 B2 | 2/2019 | Woo | |
| 10,307,452 B2 | 6/2019 | Willimann | |
| 10,357,442 B2 | 7/2019 | Schelges et al. | |
| 10,517,806 B2 * | 12/2019 | Emiru | A61K 8/416 |
| 10,549,078 B2 * | 2/2020 | Mingione | A61M 35/003 |
| 10,632,083 B2 | 4/2020 | Shabto | |
| 10,688,067 B2 | 6/2020 | Allen et al. | |
| 11,027,032 B2 | 6/2021 | Degala et al. | |
| 2003/0212005 A1 | 11/2003 | Petito et al. | |
| 2004/0185028 A1 | 9/2004 | Hu et al. | |
| 2005/0222276 A1 | 10/2005 | Schmaus et al. | |
| 2007/0087744 A1 | 4/2007 | Haglund | |
| 2008/0254150 A1 | 10/2008 | Rheins et al. | |
| 2008/0275113 A1 | 11/2008 | Huetter et al. | |
| 2008/0311070 A1 | 12/2008 | Burke et al. | |
| 2009/0042870 A1 | 2/2009 | Fellows et al. | |
| 2009/0111780 A1 | 4/2009 | Giordano | |
| 2011/0152302 A1 | 6/2011 | Razzak et al. | |
| 2013/0267490 A1 | 10/2013 | Gupta et al. | |
| 2014/0243417 A1 | 8/2014 | Modak et al. | |
| 2016/0100574 A1 * | 4/2016 | Pesaro et al. | A01N 31/04 |
| 2016/0338951 A1 | 11/2016 | Nayar | |
| 2017/0368234 A1 | 12/2017 | Modak et al. | |
| 2018/0161438 A1 | 6/2018 | Matsumura | |
| 2018/0177189 A1 | 6/2018 | Kleine et al. | |
| 2018/0353518 A1 | 12/2018 | Morishima et al. | |
| 2019/0191704 A1 | 6/2019 | Albright et al. | |
| 2019/0209466 A1 | 7/2019 | Benita et al. | |
| 2019/0282478 A1 | 9/2019 | Pesaro et al. | |
| 2020/0030499 A1 | 1/2020 | Menon et al. | |
| 2020/0237816 A1 | 7/2020 | Lait | |
| 2020/0359622 A1 | 11/2020 | Josephson et al. | |
| 2020/0375189 A1 | 12/2020 | Alimi et al. | |
| 2021/0177218 A1 | 6/2021 | Jin et al. | |

FOREIGN PATENT DOCUMENTS

| | | | | |
|---|---|---|---|---|
| CN | 104739664 A | 7/2015 | | |
| CN | 107485623 A | 12/2017 | | |
| EP | 0231080 B1 * | 5/1987 | ............... | C11D 3/00 |
| EP | 0 231 080 A1 | 8/1987 | | |
| EP | 3 574 760 A1 | 12/2019 | | |
| GB | 0231080 A1 * | 8/1987 | ............... | C11D 3/00 |
| JP | H01-104003 A | 4/1989 | | |
| WO | WO-2011/057387 A1 | 5/2011 | | |
| WO | WO-2019/006217 A1 | 1/2019 | | |

(Continued)

OTHER PUBLICATIONS

Apfelbaum et al., American Society of Anesthesiologists: Practice advisory for the prevention and management of operating room fires. Anesthesiology, 2008; 108:786-801.*
James R. Hebl, Regional Anesthesia and Pain Medicine, vol. 31, No. 4 Jul.-Aug. 2006: pp. 311-323).*
AST Standards of Practice for Surgical Drapes authored by the AST Education and Professional Standards Committee and have been approved by the AST Board of Directors, Apr. 13, 2008.*
Apfelbaum et al (Anesthesiology 2013; 118:271-90, Practice advisory for the prevention and management of operating room fires ( Year: 2013).*
James R. Hebl (The Importance and Implications of Aseptic Techniques During Regional Anesthesia., Regional Anesthesia and Pain Medicine, vol. 31, No. 4 Jul.-Aug. 2006: pp. 311-323) (Year: 2006).*

(Continued)

*Primary Examiner* — Jeffrey H Murray
*Assistant Examiner* — Luisalberto Gonzalez
(74) *Attorney, Agent, or Firm* — FOLEY & LARDNER LLP (57) ABSTRACT

A method for the preparation of a patient's skin prior to surgery includes applying a volume of an antiseptic solution to the skin surface prior to surgery in an amount effective to reduce bacteria on the skin surface; and allowing the antiseptic solution to stand on the skin surface for less than three minutes before commencing surgery. The antiseptic solution includes a biguanide and benzyl alcohol, and is comparable to an antiseptic solution containing at least 60% isopropyl alcohol or at least 60% ethyl alcohol at reducing bacteria.

20 Claims, 4 Drawing Sheets

(56) References Cited

FOREIGN PATENT DOCUMENTS

WO     WO-2019/126703 A1    6/2019
WO     WO-2020/255036 A1   12/2020

OTHER PUBLICATIONS

Association of Surgical Technologists (AST) Standards of Practice for Surgical Drapes (authored by the AST Education and Professional Standards Committee, effective from Apr. 13, 2008). (Year: 2008).*

Flammable and Combustible Liquids Code, NFPA 30, 2015 Edition was issued by the Standards Council on Apr. 29, 2014, with an effective date of May 19, 2014, This edition of NFPA 30 was approved as an American National Standard on May 19, 2014. (Year: 2014).*

Arsalan. J. Bagai Med. Univ., vol. 13, No. 2 2010 (Year: 2010).*

Chevalier et al., Evaluation of synergistic effects of three bactericidal agents associated in an antiseptic formulation, Pharmaceutica Acta Helvetiae, vol. 70, 155-159, 1995, 5 pages.

Maiwald et al., The Forgotten Role of Alcohol: A Systematic Review and Meta-Analysis of the Clinical Efficacy and Perceived Role of Chlorhexidine in Skin Antisepsis, PLoS One, vol. 7, Issue 9, Sep. 5, 2012, 12 pages.

*Sage Products, LLC* v. *Coke Morgan Stewart, et al.*, 2023-1603, 2023-1604 (Fed Cir. Apr. 15, 2025).

* cited by examiner

ANTIMICROBIAL SOLUTION FOR PRE-OPERATIVE PREPARATION

CROSS-REFERENCE TO RELATED APPLICATIONS

This application claims the benefit of and priority to U.S. Provisional Patent Application No. 63/217,023, filed Jun. 30, 2021, which is hereby incorporated by reference herein in its entirety.

BACKGROUND

The present disclosure relates generally to an antimicrobial solution (e.g., an antiseptic solution). More specifically, the present disclosure relates to an antimicrobial solution comprising a biguanide, such as chlorhexidine gluconate, as a primary active ingredient for pre-operative preparation, and to methods for preparation of a patient's skin prior to surgery.

Preoperative skin solutions are often applied to a patient's skin before a surgical operation to prevent and/or reduce surgical site infections. Alcohol-based preoperative skin solutions are often flammable. For example, alcohol-based preoperative skin solutions can pool on the patient's skin, resulting in fumes gathering under surgical drapes and an increase the susceptibility of the drapes, patient's skin or hair, and/or other surgical instruments igniting when an ignition source (i.e., electrosurgical equipment, electrocautery device, laser, etc.) is present and/or in use. The risk is especially high in an oxygen-enriched atmosphere, such as in an operating room where oxygen is in use. On the other hand, alternative preoperative skin solutions having a non-alcohol based formulation may not achieve timely killing and/or reduction of microorganisms compared to alcohol-based preoperative skin solutions.

The present disclosure seeks to overcome certain of these limitations and other drawbacks of existing alcohol-based preoperative skin solutions and/or solutions having other antimicrobial (e.g., antiseptic) ingredients, and to provide new features that are not heretofore available.

BRIEF DESCRIPTION OF THE FIGURES

The disclosure will become more fully understood from the following detailed description, taken in conjunction with the accompanying figures.

DETAILED DESCRIPTION

Before providing a detailed description of specific embodiments or turning to the Figures, which illustrate certain exemplary embodiments in detail, it should be understood that the present disclosure is not limited to the details or methodology set forth in the description or illustrated in the Figures. It should also be understood that the terminology used herein is for the purpose of description only and should not be regarded as limiting.

The present disclosure relates to antimicrobial solutions (e.g., antiseptic solutions) comprising a biguanide, such as chlorhexidine gluconate (CHG), and benzyl alcohol, and to methods for preparation of a patient's skin prior to surgery using such an antimicrobial solution. As discussed in more detail below, the antimicrobial solutions described herein exhibit advantages properties as compared to previously described antimicrobial CHG solutions, such as being non-flammable. As also discussed in more detail below, the advantages properties of the antimicrobial solutions described herein permit their use in more efficient, convenient methods, such as methods with a shorter standing time between application of the solution to a patient's skin surface and commencement of surgery than is possible with antimicrobial CHG solutions that comprise, e.g., at least 60% isopropyl alcohol or at least 60% ethyl alcohol (or at least 60% of isopropyl alcohol and ethyl alcohol combined).

The various exemplary embodiments disclosed herein relate to an antimicrobial solution (e.g, antiseptic solution) to be applied to a surface (e.g., skin, surgical surface, etc.), a method of producing the antimicrobial solution, and a method for preparation of a patient's skin prior to surgery. Further, in some exemplary embodiments, an applicator may be used to apply an antimicrobial solution to the skin. While various application devices are described, it should be understood that the present disclosure similarly applies to other types of application devices. For example, the application device may be an applicator, a swab, a wand coupled to a sponge, a wipe, a cloth, a finger applicator, or any other suitable device configured to apply a solution.

According to an exemplary embodiment, the antimicrobial solution comprises a solvent, such as water, an antimicrobial agent, such as a biguanide, and an enhancing ingredient, such as benzyl alcohol. According to another exemplary embodiment, the antimicrobial solution comprises a solvent, an antimicrobial agent, an enhancing ingredient, and a surfactant, such as lauryl glucoside. Additionally or alternatively, in some embodiments, the disclosed antimicrobial solutions optionally comprise one or more additional excipients. For example, suitable excipients may include one or more of a pH adjuster, pH buffer, film formers, colorants, preservatives, viscosity increasing agents, etc. Excipients suitable for use with the disclosed antimicrobial (e.g., antiseptic) solutions are known in the art and include, at least, those listed in *The International Cosmetic Ingredient Dictionary And Handbook*, 15$^{th}$ Edition (2013).

Referring now to Table 1 and Table 2 below, according to an exemplary embodiment, the antimicrobial solution comprises 0.5-4.0% wt. CHG, 0.5-5.0% wt. benzyl alcohol, and water. The antimicrobial solution optionally may further comprise a surfactant, such as a nonionic surfactant, such as 0.05-5.0% w/v of a nonionic surfactant, such as lauryl glucoside. The antimicrobial solution optionally may further comprise one or more pH adjusters, and may be formulated in a suitable buffer, such as a phosphate buffer (e.g., prepared with one or both of monobasic sodium phosphate and dibasic sodium phosphate). Referring to Table 2, the antimicrobial solution optionally may further comprise one or more colorants.

TABLE 1

| | Range | Purpose |
|---|---|---|
| Water | 83.0-99.4% | Solvent |
| Chlorhexidine Gluconate | 0.5-4.0% | Antimicrobial Agent |
| Benzyl Alcohol | 0.05-5.0% | Enhancing Ingredient |
| Lauryl Glucoside | 0.05-5.0% | Surfactant |
| Gluconodelta lactone (GDL) | 0-3.0% | pH Adjuster |
| Monobasic sodium phosphate | | pH Buffer |
| Dibasic sodium phosphate | | pH Buffer |

TABLE 2

| | Range | Purpose |
|---|---|---|
| Water | 78.0-99.39% | Solvent |
| Chlorhexidine Gluconate | 0.5-4.0% | Antimicrobial Agent |
| Benzyl Alcohol | 0.05-5.0% | Enhancing Ingredient |
| Lauryl Glucoside (Optional) | 0.05-5.0% | Surfactant |
| Gluconodelta lactone (GDL) (Optional) | 0-3.0% | pH Adjuster |
| Monobasic sodium phosphate (Optional) | | pH Buffer |
| Dibasic sodium phosphate (Optional) | | pH Buffer |
| Colorant (Optional) | 0.01-5.0% | Colorant |

As shown in Table 1 and Table 2, according to exemplary embodiments, the antimicrobial solution (e.g, antiseptic solution) includes a solvent. In an exemplary embodiment, the solvent is water. The water may be distilled water, sterile water, purified water prepared in accordance with the United States Pharmacopeia (USP) standards, or any other suitable type of water that is suitable for use in antimicrobial solutions. According to an exemplary embodiment, shown in Table 1, the water is included in the antimicrobial solution in the amount of from 83.0 to 99.4 wt. % based on the total weight of the antimicrobial solution. According to an exemplary embodiment, shown in Table 1, the water is included in the antimicrobial solution in the amount of from 78.0 to 99.39% wt. % based on the total weight of the antimicrobial solution. In some embodiments, the water is included in the antimicrobial solution in the amount of from 90.0 to 98.2 wt. % based on the total weight of the antimicrobial solution. In other embodiments, the water is included in the amount of from 90.5 to 98.2, of from 91.0 to 98.2, of from 91.5 to 98.2, of from 92.0 to 98.2, of from 92.5 to 98.2, of from 93.0 to 98.2, of from 93.5 to 98.2, of from 94.0 to 98.2, of from 94.5 to 98.2, of from 95.0 to 98.2, of from 95.5 to 98.2, of from 96.0 to 98.2, of from 96.5 to 98.2, of from 97.0 to 98.2, of from 97.5 to 98.2, or of from 98.0 to 98.2 wt. % based on the total weight of the antimicrobial solution. In yet other embodiments, the solvent comprises an aqueous solvent, a non-aqueous solvent, or a combination thereof. It should be understood that the amount of solvent may vary outside the ranges above; however, in an exemplary embodiment the solvent is whole and/or fractional values within these ranges. Further, it should be understood that more than one solvent may be included in the antimicrobial solution, in which case the total amount of all the solvents included in the antimicrobial solution may be within the ranges discussed in Table 1 and Table 2. While exemplary amounts of water in the composition are disclosed, it should be understood that the amount of water will depend on the amount of other components present. Thus, if the optional components are present or if additional components not mentioned herein are present, the amount of water may vary from the exemplary ranges disclosed.

As shown in Table 1 and Table 2, according to exemplary embodiments, the antimicrobial solution (e.g., antiseptic solution) also includes an antimicrobial agent. In an exemplary embodiment, the antimicrobial agent is chlorhexidine gluconate (1,6-bis(4-chloro-phenylbiguanide) hexane). According to an exemplary embodiment, the chlorhexidine gluconate is included in the antimicrobial solution in the amount of from 0.5 to 4.0 wt. % based on the total weight of the antimicrobial solution. In some embodiments, the chlorhexidine gluconate is included in the antimicrobial solution in the amount of from 1.0 to 4.0 wt. % based on the total weight of the antimicrobial solution. In yet other embodiments, the chlorhexidine gluconate is included in the antimicrobial solution in the amount of from 1.5 to 4.0, of from 2.0 to 4.0, of from 2.5 to 4.0, of from 3.0 to 4.0, or of from 3.5 to 4.0 wt. % based on the total weight of the antimicrobial solution. In still other embodiments, the chlorhexidine gluconate is included in the antimicrobial solution in the amount of from 0.5 to 3.5, of from 0.5 to 3.0, of from 0.5 to 2.5, of from 0.5 to 2.0, of from 0.5 to 1.5, or of from 0.5 to 1.0 wt. % based on the total weight of the antimicrobial solution. While exemplary amounts of CHG are disclosed, it should be understood that other biguanide and/or bis-biguanide antimicrobial agents can be used. In such embodiments, amounts of the biguanide and/or bis-biguanide antimicrobial agent(s) equivalent to the amounts disclosed for CHG can be used, e.g., based on molecular weight, optionally accounting for any difference in antimicrobial potency. It should be understood that the amount of the antimicrobial agent may vary outside the ranges above; however, in an exemplary embodiment the antimicrobial agent is whole and/or fractional values within these ranges. Further, it should be understood that more than one antimicrobial agent may be included in the antimicrobial solution, in which case the total amount of all the antimicrobial agent included in the antimicrobial solution may be within the ranges discussed in Table 1 and 2.

As shown in Table 1 and Table 2, according to exemplary embodiments, the antimicrobial solution (e.g, antiseptic solution) also includes an ingredient that enhances the efficacy of the formulation. In an exemplary embodiment, the enhancing ingredient is benzyl alcohol (phenol methanol, phenolcarbinol, benzenemethanol). According to an exemplary embodiment, the benzyl alcohol is included in the antimicrobial solution in the amount of from 0.05 to 3.0 or of from 0.05 to 5.0 wt. % based on the total weight of the antimicrobial solution. In some embodiments, the benzyl alcohol is included in the antimicrobial solution in the amount of from 0.10 to 3.0 wt. % based on the total weight of the antimicrobial solution. In yet other embodiments, the benzyl alcohol is included in the antimicrobial solution in the amount of from 0.25 to 3.0, of from 0.5 to 3.0, of from 1.0 to 3.0, of from 1.5 to 3.0, of from 2.0 to 3.0, or of from 2.5 to 3.0 wt. % based on the total weight of the antimicrobial solution. It should be understood that the amount of the enhancing ingredient may vary outside the ranges above; however, in an exemplary embodiment the enhancing ingredient is whole and/or fractional values within these ranges.

As shown in Table 1 and Table 2, according to some embodiments, the antimicrobial solution (e.g., antiseptic solution) also includes a surfactant. In an exemplary embodiment, the surfactant is lauryl glucoside (dodecyl glucoside, lauryl polyglucoside, Dodecyl β-D-glucopyranoside). According to an exemplary embodiment, the lauryl glucoside is included in the antimicrobial solution in the amount of from 0.05 to 2.5 or of from 0.05 to 5.0 wt. % based on the total weight of the antimicrobial solution. In some embodiments, the lauryl glucoside is included in the antimicrobial solution in the amount of from 0.10 to 2.5 wt. % based on the total weight of the antimicrobial solution. In other embodiments, the lauryl glucoside is included in the antimicrobial solution in the amount of from 0.25 to 2.5, of from 0.50 to 2.5, of from 0.75 to 2.5, of from 1.0 to 2.5, of from 1.25 to 2.5, of from 1.5 to 2.5, of from 1.75 to 2.5, of from 2.0 to 2.5, or of from 2.25 to 2.5 wt. % based on the total weight of the antimicrobial solution. In some embodiments, the surfactant is an alkyl glucoside, alkyl polyglucoside, or another suitable non-ionic surfactant. In other embodiments, the surfactant may be any other surfactant that is compatible with the antimicrobial agent. It should be understood that the amount of surfactant may vary outside the ranges above; however, in an exemplary embodiment the surfactant is whole and/or fractional values within these ranges. Further, it should be understood that more than one surfactant may be included in the antimicrobial solution, in which case the total amount of all the surfactants included in the antimicrobial solution may be within the ranges discussed in Table 2.

As shown in Table 1 and Table 2, according to some embodiments, the antimicrobial solution (e.g., antiseptic solution) also includes at least one of a pH adjuster or a pH booster. In an exemplary embodiment, the pH adjuster is gluconodelta lactone (gluconolactone, D-Glucono-1, 5-lactone). According to an exemplary embodiment, the gluconodelta lactone is included in the antimicrobial solution in the amount of from 0 to 3.0 wt. % based on the total weight of the antimicrobial solution. In some embodiments, the gluconodelta lactone is included in the antimicrobial solution in the amount of from 0.05 to 3.0 wt. % based on the total weight of the antimicrobial solution. In yet other embodiments, the gluconodelta lactone is included in the antimicrobial solution in the amount of from 1.0 to 3.0, of from 1.5 to 3.0, of from 2.0 to 3.0, or of from 2.5 to 3.0 wt. % based on the total weight of the antimicrobial solution. In some embodiments, the pH adjuster is an acidifier, sequestrant, chelating agent, or any other suitable pH adjuster. In other embodiments, the pH adjuster may be any other pH adjuster that is compatible with the antimicrobial solution. It should be understood that the amount of the pH adjuster may vary outside the ranges above; however, in an exemplary embodiment the pH adjuster is whole and/or fractional values within these ranges. Further, it should be understood that more than one pH adjuster may be included in the antimicrobial solution, in which case the total amount of all the pH adjuster included in the antimicrobial solution may be within the ranges discussed in Table 1 and Table 2.

According to some embodiments, the antimicrobial solution is formulated with a buffer, such as a phosphate buffer. Thus, according to some embodiments, the pH buffer is at least one of monobasic sodium phosphate and dibasic sodium phosphate. In some embodiments, the pH buffer is sodium dihydrogen orthophosphate, sodium dihydrogen phosphate, sodium phosphate monobasic, disodium phosphate hydrate, monohydrate dibasic sodium phosphate, or another suitable pH buffer. According to an exemplary embodiment, the monobasic sodium phosphate and/or the monobasic sodium phosphate is included in an amount based on the total weight of the antimicrobial solution. It should be understood that in some embodiments no pH buffer (e.g., monobasic sodium phosphate, dibasic sodium phosphate, etc.) is included in the antimicrobial solution. It should also be understood that in other embodiments more than one pH buffer may be included in the antimicrobial solution.

It should be understood that the ranges provided above for each of the components of the antimicrobial solution (e.g., the solvent, antimicrobial agent, the enhancing ingredient, the surfactant, the pH adjuster, the pH buffers, etc.) may refer to amounts in the sterilized antimicrobial compositions or the unsterilized antimicrobial compositions. In this regard, because certain sterilization processes may cause certain components to degrade, the amount of each component in the antimicrobial solution may vary from the non-sterile to the sterilized condition. For example, the antimicrobial solution discussed above should be understood to encompass the possibility that the sterilized antimicrobial solution may comprise an amount of from 0.5 to 4.0 wt. % of the antimicrobial agent, or alternatively, that the unsterilized antimicrobial solution may comprise an amount of from 0.5 to 4.0 wt. % of the antimicrobial agent.

In one exemplary embodiment, the antimicrobial solution comprises 2% chlorhexidine gluconate, 2% benzyl alcohol, and water. In another exemplary embodiment, the antimicrobial solution comprises 2% chlorhexidine gluconate, 2% benzyl alcohol, 2% lauryl glucoside, and water.

According to an exemplary embodiment, the antimicrobial solution (e.g, antiseptic solution) is non-flammable. In this regard, an antimicrobial solution comprising certain antimicrobial agents (e.g., chlorhexidine gluconate, 1,6-bis (4-chloro-phenylbiguanide) hexane, cationic antimicrobial agent (or a antimicrobial agent), biguanide, bis-biguanide, etc.) may reduce the potential risk of fire that may be associated with other antimicrobial solutions (e.g., those that contain ethanol, isopropyl alcohol, etc.). Flammability is of particular concern in a surgical setting where oxygen may be used or may be in use, and/or where an ignition source may be present and/or in use, such as one or more of electrosurgical equipment, electrocautery equipment, and lasers.

According to OSHA, flammability in the general industry is defined as "any liquid having a flashpoint at or below 199.4° F. (93° C.)." (29 CFR 1910.106 (a) (19)). Flammability testing was carried out on certain exemplary embodiments: GOL-1 which consists essentially of (i.e., has as its principal ingredients) 2% chlorhexidine gluconate and 2% benzyl alcohol, and GOL-2 which consists essentially of (i.e., has as its principal ingredients) 2% chlorhexidine gluconate, 2% benzyl alcohol, and 2% lauryl glucoside. The testing was performed in accordance with ASTM D93, *Standard Test Methods for Flash Point by Pensky-Martens Closed Cup Tester* (2018), which determines the lowest temperature at which application of a test flame causes vapors of a sample to ignite under specified test conditions. A sample is deemed to have flashed when a flame appears and instantaneously propagates over the surface of the sample. In the testing of GOL-1 and GOL-2, no flash was observed prior to the sample boiling. Accordingly, the testing confirmed that GOL-1 and GOL-2 are non-flammable. In contrast, compositions that contain 70% isopropyl alcohol come with a flammability warning, and 70% isopropyl alcohol has a known flash point of approximately 65° F. (approximately 18° C.).

Furthermore, while the antimicrobial solution (e.g., antiseptic solution) is non-flammable, the antimicrobial solution also maintains adequate effectiveness and/or timeliness for killing and/or reducing microorganisms at a surface (e.g., the skin). For example, some antimicrobial solutions may achieve timely and effective killing and/or reduction of microorganisms; however, these antimicrobial solutions contain components that make the solution flammable (e.g., 70% isopropanol, etc.). Conversely, other antimicrobial solutions remove the flammable component; however, contain components (e.g., only a solvent and an antimicrobial agent, for example water and 2% chlorhexidine gluconate) that may not achieve the most timely and effective killing and/or reduction of microorganisms. In this regard, according to an exemplary embodiment, the antimicrobial solution discussed herein removes components that make the solution flammable (e.g., 70% isopropanol, etc.), while also maintaining (or increasing) effectiveness and timeliness of/in killing and/or reducing microorganisms at a surface (e.g., the skin) compared to other antimicrobial solutions, for example, as compared to a solution comprising 70% isopropanol and 2% chlorhexidine gluconate, as shown in the testing results in Tables 3-5 below.

The in vitro testing data presented in the following Tables 3-5 was obtained utilizing testing procedures according to ASTM E2783-11 (2016), *Standard Test Method for Assessment of Antimicrobial Activity for Water Miscible Compounds Using a Time-Kill Procedure*. This test method measures the changes of a population of aerobic and anaerobic microorganisms within a specific sampling time when tested against antimicrobial test materials in vitro (i.e., in a test tube). The results at each sampling time (i.e., at 15 seconds, 30 seconds, and 3 minutes after exposure) are presented in log reduction, a mathematical term that is used to express the relative number of living microbes that are reduced by disinfection. A log reduction of 1 represents a reduction factor of 10, or a 90% reduction. A log reduction of 5 represents a reduction factor of 100,000 or a 99.999% reduction. As used herein, a property of being "effective at reducing bacteria" (or microorganisms generally) can be assessed by ASTM E2783-11 (2016), *Standard Test Method for Assessment of Antimicrobial Activity for Water Miscible Compounds Using a Time-Kill Procedure*. Thus, as used herein, the term "reduce" bacteria refers to killing bacteria.

In exemplary embodiments, the antiseptic solution is comparable to an antiseptic solution containing at least 60% isopropyl alcohol or at least 60% ethyl alcohol (or at least 60% of isopropyl alcohol and ethyl alcohol combined) in reducing bacteria. For example, the antiseptic solution may achieve a log reduction of bacteria that is greater than or equal to X−0.5 log 10, where X is the log reduction achieved by an antiseptic solution containing at least 60% isopropyl alcohol or at least 60% ethyl alcohol, such as when tested as described above and illustrated below.

Tables 3-1a, 3-1b, and 3-1c, below, present the in vitro testing data of various antiseptic compositions against *Enterococcus faecalis* bacteria. Tables 3-2a and 3-2b, below, present the in vitro testing data of various antiseptic compositions against Methicillin-resistant *Staphylococcus aureus* (MRSA) bacteria. Concentrations of certain ingredients in the various compositions are noted, including the concentrations of chlorhexidine gluconate (CHG), benzyl alcohol (BA) (enhancing ingredient), lauryl glucoside (LG) (surfactant), gluconodelta lactone (GDL) (pH adjuster), and isopropyl alcohol (IPA). As shown, GOL-1 and GOL-2 are at least comparable to (e.g., at least as effective as) a formulation which includes 70% isopropyl alcohol (IPA) at reducing bacteria, and significantly more effective than other CHG formulations.

TABLE 3-1a

| Formulation | Log reduction @ Time | | | Composition | | | | |
|---|---|---|---|---|---|---|---|---|
| | 15 sec | 30 sec | 3 min | % CHG | % BA | % LG | % GDL | % IPA |
| 2% CHG/70% IPA | 6.47 | 6.47 | 6.47 | 2 | 0 | 0 | 0 | 70 |
| GOL-1 | 6.47 | 6.47 | 6.47 | 2 | 2 | 0 | 0 | 0 |
| GOL-2 | 6.47 | 6.47 | 6.47 | 2 | 2 | 2 | 0.1014 | 0 |

TABLE 3-1b

| Formulation | Log reduction @ Time | | | Composition | | | | |
|---|---|---|---|---|---|---|---|---|
| | 15 sec | 30 sec | 3 min | % CHG | % BA | % LG | % GDL | % IPA |
| 2% CHG & water | 0 | 0 | 0.76 | 2 | 0 | 0 | 0 | 0 |
| 4% CHG & water | 0 | 0 | 0 | 4 | 0 | 0 | 0 | 0 |
| 2% CHG/0.10% GDL | 0 | 0 | 0.36 | 2 | 0 | 0 | 0.1 | 0 |
| Isopropanol | 5.68 | 5.68 | 5.68 | 0 | 0 | 0 | 0 | 70 |
| Marketed 2% CHG | 0 | 0.07 | 0.26 | 2 | 0 | 0 | <.1 | 0 |

TABLE 3-1c

| Formulation | Log reduction @ Time | | | Composition | | | | |
|---|---|---|---|---|---|---|---|---|
| | 15 sec | 30 sec | 3 min | % CHG | % BA | % LG | % GDL | % IPA |
| Marketed 2% CHG | — | 0 | 0.02 | 2 | 0 | 0 | <.1 | 0 |
| 2% CHG/2% LG | — | 0.03 | 5.22 | 2 | 0 | 2 | 0 | 0 |
| GOL-2 | — | 5.59 | 5.59 | 2 | 2 | 2 | 0.1014 | 0 |
| GOL-1 | — | 5.59 | 5.59 | 2 | 2 | 0 | 0 | 0 |

TABLE 3-2a

| Formulation | Log reduction @ Time | | | Composition | | | | |
|---|---|---|---|---|---|---|---|---|
| | 15 sec | 30 sec | 3 min | % CHG | % BA | % LG | % GDL | % IPA |
| 2% CHG & water | 0.87 | 1.3 | 5.14 | 2 | 0 | 0 | 0 | 0 |
| 4% CHG & water | 0.99 | 1.2 | 3.38 | 4 | 0 | 0 | 0 | 0 |

TABLE 3-2a-continued

| | Log reduction @ Time | | | Composition | | | | |
|---|---|---|---|---|---|---|---|---|
| Formulation | 15 sec | 30 sec | 3 min | % CHG | % BA | % LG | % GDL | % IPA |
| 2% CHG/0.10% GDL | 0.92 | 1.21 | 4.47 | 2 | 0 | 0 | 0.1 | 0 |
| Isopropanol | 5.15 | 5.15 | 5.15 | 0 | 0 | 0 | 0 | 70 |
| Marketed 2% CHG | 1.21 | 1.84 | 5.15 | 2 | 0 | 0 | <.1 | 0 |

TABLE 3-2b

| | Log reduction @ Time | | | Composition | | | | |
|---|---|---|---|---|---|---|---|---|
| Formulation | 15 sec | 30 sec | 3 min | % CHG | % BA | % LG | % GDL | % IPA |
| Marketed 2% CHG | — | 3.15 | 5.07 | 2 | 0 | 0 | <.1 | 0 |
| 2% CHG/2% LG | — | 5.23 | 5.23 | 2 | 0 | 2 | 0 | 0 |
| GOL-2 | — | 5.23 | 5.23 | 2 | 2 | 2 | 0 | 0 |
| GOL-1 | — | 6.15 | 6.15 | 2 | 2 | 0 | 0 | 0 |

Tables 4-1, 4-2, and 4-3 below, present the in vitro testing data of a marketed 2% CHG product (which includes 2% CHG, 0.1% GDL, water, Nonoxynol-9, Polysorbate 20, Dimethicone, Fragrance, Propylene Glycol, Aloe Vera, and Glycerin), GOL-2, and 2% CHG/70% IPA compositions against various microorganisms (e.g., bacteria, fungi, and yeast) at 15 seconds, 30 seconds, and 3 minutes, respectively. As shown, GOL-2 is at least comparable to (e.g., at least as effective as) a formulation which includes 70% isopropyl alcohol (IPA) at reducing bacteria, and significantly more effective at early testing intervals than the marketed CHG product.

TABLE 4-1

15 SECONDS

| | Marketed 2% CHG | GOL-2 | 2% CHG/ 70% IPA |
|---|---|---|---|
| A. baumannii | 2.48 | 5.78 | 5.78 |
| B. fragilis | 5.33 | 6.59 | 6.59 |
| C. albicans | 0.91 | 5.13 | 5.13 |
| C. tropicalis | 4.61 | 4.71 | 4.71 |
| E. faecium VRE, MDR | 0.03 | 5.22 | 5.22 |
| E. faecium | 0.04 | 5.21 | 5.21 |
| E. faecium, VRE | 0.04 | 5.33 | 5.33 |
| E. coli | 5 | 5 | 5 |
| H. influenzae | 4.4 | 4.4 | 4.4 |
| K. pneumonaiae | 4.71 | 4.87 | 5.16 |
| K. pneumonaiae KPC | 4.6 | 5.11 | 5.11 |
| Klebsiella species | 4.97 | 5.45 | 5.45 |
| M. yunnanesis | 6.37 | 6.37 | 6.37 |
| P. miribalis | 2.61 | 5.51 | 5.51 |
| P. aeruginosa | 5.17 | 5.17 | 5.17 |
| S. marcescens | 1.67 | 5.42 | 5.42 |
| S. aureus | 1.43 | 5.2 | 5.2 |
| S. aureus MRSA | 1.4 | 4.93 | 4.93 |
| S. epidermidis | 3.72 | 5.33 | 5.33 |
| S. epidermidis MRSE | 3.44 | 4.99 | 4.99 |
| S. haemolyticus | 3.88 | 4.63 | 4.63 |
| S. hominis | 5.11 | 5.11 | 5.11 |
| S. saprphyticus | 4.8 | 4.8 | 4.8 |
| S. pneumoniae | 0.03 | 5.96 | 5.96 |
| S. pyogenes | 0.63 | 4.7 | 4.7 |

TABLE 4-2

30 SECONDS

| | Marketed 2% CHG | GOL-2 | 2% CHG/ 70% IPA |
|---|---|---|---|
| A. baumannii | 2.95 | 5.78 | 5.78 |
| B. fragilis | 6.59 | 6.59 | 6.59 |
| C. albicans | 1.31 | 5.13 | 5.13 |
| C. tropicalis | 4.71 | 4.71 | 4.71 |
| E. faecium VRE, MDR | 0.1 | 5.22 | 5.22 |
| E. faecium | 0.09 | 5.21 | 5.21 |
| E. faecium, VRE | 0.01 | 5.33 | 5.33 |
| E. coli | 5 | 5 | 5 |
| H. influenzae | 4.4 | 4.4 | 4.4 |
| K. pneumonaiae | 5.16 | 5.16 | 5.16 |
| K. pneumonaiae KPC | 5.11 | 4.88 | 5.11 |
| Klebsiella species | 5.45 | 5.45 | 5.45 |
| M. yunnanesis | 6.37 | 6.37 | 6.37 |
| P. miribalis | 3.43 | 5.51 | 5.51 |
| P. aeruginosa | 5.17 | 5.17 | 5.17 |
| S. marcescens | 4.14 | 5.42 | 5.42 |
| S. aureus | 1.89 | 5.2 | 5.2 |
| S. aureus MRSA | 2.27 | 4.93 | 4.93 |
| S. epidermidis | 5.35 | 5.33 | 5.33 |
| S. epidermidis MRSE | 4.93 | 4.99 | 4.99 |
| S. haemolyticus | 4.26 | 4.63 | 4.63 |
| S. hominis | 5.11 | 5.11 | 5.11 |
| S. saprphyticus | 4.8 | 4.8 | 4.8 |
| S. pneumoniae | 0.06 | 5.96 | 5.96 |
| S. pyogenes | 1.57 | 4.7 | 4.7 |

TABLE 4-3

3 MINUTES

| | Marketed 2% CHG | GOL-2 | 2% CHG/ 70% IPA |
|---|---|---|---|
| A. baumannii | 5.78 | 5.78 | 5.78 |
| B. fragilis | 6.59 | 6.59 | 6.59 |
| C. albicans | 3.04 | 5.13 | 5.13 |
| C. tropicalis | 4.71 | 4.71 | 4.71 |
| E. faecium VRE, MDR | 0.28 | 5.22 | 5.22 |
| E. faecium | 1.96 | 5.21 | 5.21 |
| E. faecium, VRE | 0.18 | 5.33 | 5.33 |
| E. coli | 5 | 5 | 5 |
| H. influenzae | 4.4 | 4.4 | 4.4 |
| K. pneumonaiae | 5.16 | 5.16 | 5.16 |
| K. pneumonaiae KPC | 5.11 | 5.11 | 5.11 |
| Klebsiella species | 5.45 | 5.45 | 5.45 |
| M. yunnanesis | 6.37 | 6.37 | 6.37 |
| P. miribalis | 5.51 | 5.51 | 5.51 |
| P. aeruginosa | 5.17 | 5.17 | 5.17 |
| S. marcescens | 5.42 | 5.42 | 5.42 |
| S. aureus | 3.47 | 5.2 | 5.2 |
| S. aureus MRSA | 4.07 | 4.93 | 4.93 |
| S. epidermidis | 5.35 | 5.33 | 5.33 |
| S. epidermidis MRSE | 4.99 | 4.99 | 4.99 |
| S. haemolyticus | 4.63 | 4.63 | 4.63 |
| S. hominis | 5.11 | 5.11 | 5.11 |
| S. saprphyticus | 4.8 | 4.8 | 4.8 |
| S. pneumoniae | 3.73 | 5.96 | 5.96 |
| S. pyogenes | 2.7 | 4.7 | 4.7 |

Table 5, below, presents the in vitro testing data of a marketed 2% CHG product (which includes 2% CHG, 0.1% GDL, water, Nonoxynol-9, Polysorbate 20, Dimethicone, Fragrance, Propylene Glycol, Aloe Vera, and Glycerin), GOL-1, and 2% CHG/70% IPA compositions against various microorganisms (e.g., bacteria, fungi, and yeast) at 15 seconds and 30 seconds. As shown, GOL-1 is at least comparable to a formulation which includes 70% isopropyl alcohol at reducing bacteria, and significantly more effective than the marketed CHG product.

|  |  | 15 sec | 30 sec |
|---|---|---|---|
| Yeast |  |  |  |
| Candida albicans | Marketed 2% CHG | 0.39 | 0.75 |
|  | GOL-1 | 5.8 | 6.08 |
|  | 2% CHG/70% IPA | 6.08 | 6.08 |
| CHG resistant G(−) |  |  |  |
| B. cepacia | Marketed 2% CHG | 0.08 | 0.08 |
|  | GOL-1 | 6.11 | 6.11 |
|  | 2% CHG/70% IPA | 6.11 | 6.11 |
| G(+) |  |  |  |
| E. faecium (VRE MDR) | Marketed 2% CHG | 0.14 | 0.09 |
|  | GOL-1 | 6.71 | 6.71 |
|  | 2% CHG/70% IPA | 6.71 | 6.71 |
| G(+) |  |  |  |
| E. faecium (102618VREfm2) | Marketed 2% CHG | 0 | 0.02 |
|  | GOL-1 | 6.37 | 6.37 |
|  | 2% CHG/70% IPA | 6.37 | 6.37 |
| G(+) |  |  |  |
| E. faecium (102618VREfm3) | Marketed 2% CHG | 0.04 | 0.05 |
|  | GOL-1 | 6.72 | 6.72 |
|  | 2% CHG/70% IPA | 6.72 | 6.72 |
| G(−) |  |  |  |
| A. baumanii | Marketed 2% CHG | 2.62 | 4.02 |
|  | GOL-1 | 6.91 | 6.91 |
|  | 2% CHG/70% IPA | 6.91 | 6.91 |
| G(−) |  |  |  |
| B. fragilis | Marketed 2% CHG | 5.13 | 5.13 |
|  | GOL-1 | 5.13 | 5.13 |
|  | 2% CHG/70% IPA | 5.13 | 5.13 |
| G(+) |  |  |  |
| E. faecalis | Marketed 2% CHG | 0.14 | 0.19 |
|  | GOL-1 | 6.61 | 6.61 |
|  | 2% CHG/70% IPA | 6.61 | 6.61 |
| G(−) |  |  |  |
| P. mirabilis | Marketed 2% CHG | 3.45 | 4.08 |
|  | GOL-1 | 6.29 | 6.29 |
|  | 2% CHG/70% IPA | 6.29 | 6.29 |
| G(−) |  |  |  |
| S. marecescens | Marketed 2% CHG | 3.66 | 4.73 |
|  | GOL-1 | 6.28 | 6.28 |
|  | 2% CHG/70% IPA | 6.28 | 6.28 |
| G(+) |  |  |  |
| S. aureus (ATCC #6538) | Marketed 2% CHG | 1.23 | 1.77 |
|  | GOL-1 | 6.01 | 6.01 |
|  | 2% CHG/70% IPA | 6.01 | 6.01 |
| G(+) |  |  |  |
| S. aureus MRSA | Marketed 2% CHG | 0.58 | 1.17 |
|  | GOL-1 | 6.18 | 6.18 |
|  | 2% CHG/70% IPA | 6.18 | 6.18 |
| G(+) |  |  |  |
| S. epidermidis MRSE | Marketed 2% CHG | 3.44 | 5.59 |
|  | GOL-1 | 6.15 | 6.15 |
|  | 2% CHG/70% IPA | 6.15 | 6.15 |
| G(+) |  |  |  |
| S. haemolyticus | Marketed 2% CHG | 1.31 | 2.13 |
|  | GOL-1 | 1.99 | 2.17 |
|  | 2% CHG/70% IPA | 5.65 | 5.65 |

G(+) = gram positive;
G(−) = gram negative

The foregoing shows that the antimicrobial solutions described herein, e.g., comprising a biguanide, benzyl alcohol, and water, are comparable to an antiseptic composition that contains at least 60% isopropyl alcohol in reducing bacteria. For example, the antiseptic solution may achieve a log reduction of bacteria that is greater than or equal to X−0.5 log 10, where X is the log reduction achieved by an antiseptic solution containing at least 60% isopropyl alcohol or at least 60% ethyl alcohol (or at least 60% of isopropyl alcohol and ethyl alcohol combined).

In an illustrative example, an antimicrobial (e.g., antiseptic) solution includes at least an antimicrobial agent, an enhancing ingredient, and a surfactant. According to an exemplary embodiment, the antimicrobial agent is a biguanide, such as chlorhexidine gluconate, which may be included in the antimicrobial solution in an amount of from 0.5 to 4.0 wt. % based on the total weight of the antimicrobial solution (e.g., 2.0%, etc.). According to an exemplary embodiment, the enhancing ingredient is benzyl alcohol and is included in the antimicrobial solution in an amount of from 0.05 to 3.0 wt. % based on the total weight of the antimicrobial solution (e.g., 2.0%, etc.). In an illustrative example, such an antimicrobial solution is at least comparable to an antiseptic solution containing at least 60% isopropyl alcohol or at least 60% ethyl alcohol (or at least 60% of isopropyl alcohol and ethyl alcohol combined) in reducing bacteria. For example, such an antimicrobial solution may be highly effective for reducing microorganisms (including bacteria) on a surface (e.g., on a skin surface) to which it is applied, and exhibits the same or increased effectiveness in and timeliness of reducing microorganisms present on the surface as compared to other antimicrobial solutions, for example, as compared to a solution comprising 70% isopropanol and 2% CHG. In an illustrative example, such an antimicrobial solution additionally or alternative is non-flammable. As shown above, the exemplary embodiment of GOL-1, which consists essentially of (i.e., has as its primary active ingredients) 2% wt. CHG and 2% wt. benzyl alcohol (and water), is both at least comparable to an antiseptic solution comprising 70% isopropanol and 2% CHG at reducing bacteria, and is non-flammable.

In another illustrative example, an antimicrobial (e.g., antiseptic) solution includes at least an antimicrobial agent, an enhancing ingredient, and a surfactant. According to an exemplary embodiment, the antimicrobial agent is a biguanide, such as chlorhexidine gluconate, which may be included in the antimicrobial solution in an amount of from 0.5 to 4.0 wt. % based on the total weight of the antimicrobial solution (e.g., 2.0%, etc.). According to an exemplary embodiment, the enhancing ingredient is benzyl alcohol and is included in the antimicrobial solution in an amount of from 0.05 to 3.0 wt. % based on the total weight of the antimicrobial solution (e.g., 2.0%, etc.). In an exemplary embodiment, the surfactant is lauryl glucoside and is included in the antimicrobial solution in an amount of from 0.05 to 2.5 wt. % based on the total weight of the antimicrobial solution (e.g., 2.0%, etc.). In an illustrative example, such an antimicrobial solution is at least comparable to (e.g., at least as effective as) an antiseptic solution containing at least 60% isopropyl alcohol or at least 60% ethyl alcohol at reducing bacteria. For example, such an antimicrobial solution may be highly effective for reducing microorganisms (including bacteria) on a surface (e.g., on a skin surface) to which it is applied, and exhibits the same or increased effectiveness in and timeliness of reducing microorganisms present on the surface as compared to other antimicrobial solutions, for example, as compared to a solution comprising 70% isopropanol and 2% CHG. In an illustrative example, such an antimicrobial solution additionally or alternative is non-flammable. As shown above, the exemplary embodiment of GOL-2, which consists essentially of (i.e., has as its primary active ingredients) 2% wt. CHG, 2% wt. benzyl alcohol, and 2% lauryl glucoside (and water), is both at least comparable to (e.g., at least as effective as) an antiseptic solution comprising 70% isopropanol and 2% CHG at reducing bacteria, and is non-flammable. An antimicrobial solution (e.g., antiseptic solution) as described herein can be prepared by any suitable method, e.g., by combining the components in a suitable vessel, e.g., with stirring. Optionally, the solution can be sterilized, such as by sterilization methods that are known in the field.

Figure 1:
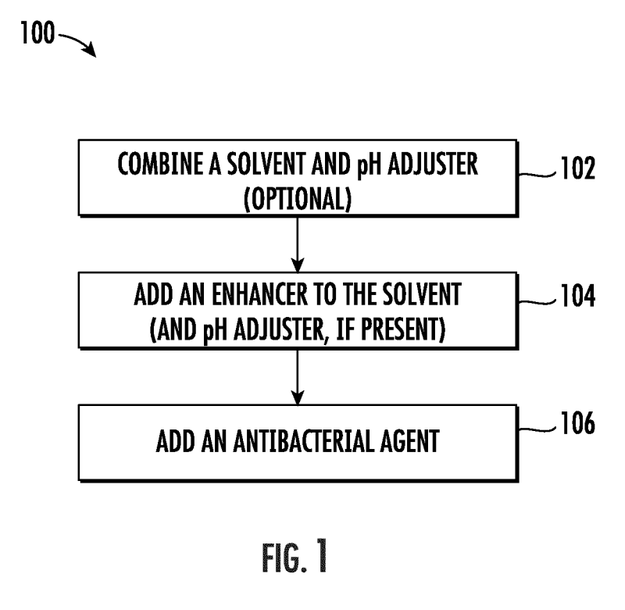
FIG. 1 is a block diagram of a process for producing an antimicrobial solution, according to an exemplary embodiment.

Referring now to FIG. 1, a non-limiting exemplary process 100 for producing an antimicrobial solution (e.g., antiseptic solution) as described herein is shown, according to an exemplary embodiment. For exemplary purposes, the antimicrobial solution may be the antimicrobial solution discussed above and/or in Table 1 or Table 2. In other embodiments, the antimicrobial solution is another suitable antimicrobial solution (e.g., including other formulations, etc.), as discussed above.

At optional initial step 102, a solvent and a pH adjuster or pH buffer are combined (e.g., added, mixed, stirred, etc.). In some embodiments of the antimicrobial solution, no pH adjuster or pH buffer are used. According to an exemplary embodiment, the pH adjuster is gluconodelta lactone. In an exemplary embodiment, the gluconodelta lactone is included in the antimicrobial solution in the amount of from 0 to 3.0 wt. % based on the total weight of the antimicrobial solution (e.g., 0.10%, etc.).

At step 104, an enhancing ingredient is added to the solvent and pH adjuster or pH buffer (if present). In an exemplary embodiment, after the solvent and the pH adjuster (or pH buffer) are combined (e.g., mixed at step 102), the enhancing ingredient is added to (e.g., combined with, mixed, stirred, etc.) the solvent and pH adjuster (or pH buffer). According to an exemplary embodiment, the enhancing ingredient is benzyl alcohol. In an exemplary embodiment, the benzyl alcohol is included in the antimicrobial solution in the amount of from 0.05 to 3.0 wt. % based on the total weight of the antimicrobial solution (e.g., 2.0%, etc.). In other embodiments, the enhancing ingredient is not benzyl alcohol; rather, the enhancing ingredient is any aromatic alcohol, preservative, or any other suitable enhancing ingredient.

At step 106, an antimicrobial agent is added to the solvent, pH adjuster or buffer (if present), and enhancing ingredient. In an exemplary embodiment, after the solvent, pH adjuster or buffer, and enhancing ingredient are combined (e.g., mixed at step 104), the antimicrobial agent is added to (e.g., combined with, mixed, stirred, etc.) the solvent, pH adjuster or buffer, and enhancing ingredient. According to an exemplary embodiment, the antimicrobial agent is chlorhexidine gluconate. In an exemplary embodiment, the chlorhexidine gluconate is included in the antimicrobial solution in the amount of from 0.5 to 4.0 wt. % based on the total weight of the antimicrobial solution (e.g., 2.0%, etc.). In other embodiments, the chlorhexidine gluconate is included in the antimicrobial solution in another amount wt. % based on the total weight of the antimicrobial solution (e.g., 9.82%, etc.). In yet other embodiments, the antimicrobial agent is not chlorhexidine gluconate; rather, the antimicrobial agent is 1,6-bis(4-chloro-phenylbiguanide) hexane, cationic antimicrobial agent (or just antimicrobial), biguanide, bis-biguanide, or any other suitable antimicrobial agent.

In some embodiments, following step 106 a pH level of the antimicrobial solution (e.g., of steps 102-106) is obtained. In yet other embodiments, a plurality of pH levels of the antimicrobial solution (e.g., of steps 102-106) is obtained (e.g., at a first time, at a second time, at a third time, etc.). A pH buffer may be added to adjust the pH.

Figure 2:
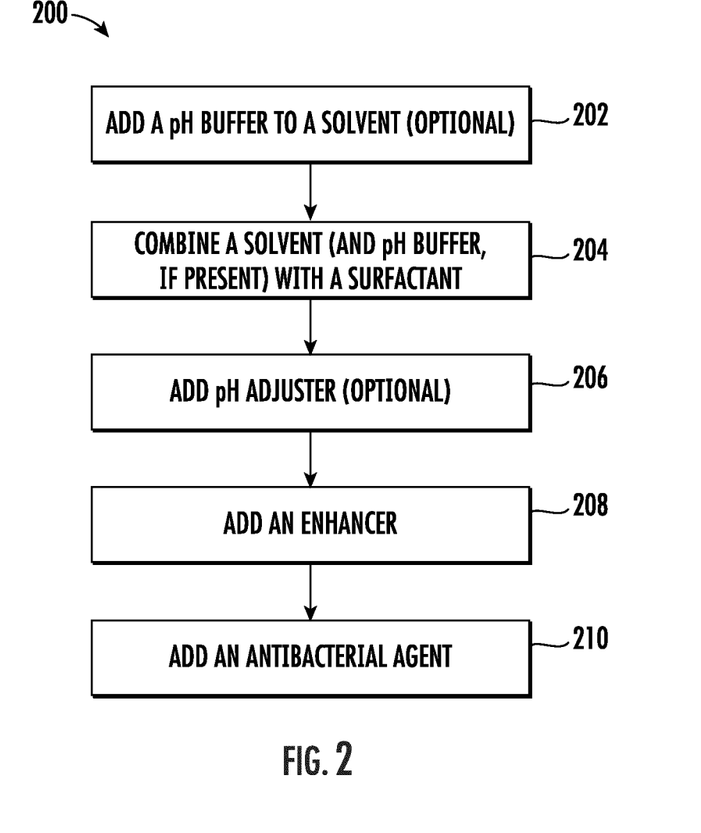
FIG. 2 is a block diagram of a process for producing an antimicrobial solution, according to another exemplary embodiment.

Referring now to FIG. 2, a process 200 for producing an antimicrobial solution (e.g., antiseptic solution) is shown, according to an exemplary embodiment. For exemplary purposes, the antimicrobial solution may be the antimicrobial solution discussed above and/or in Table 1 or Table 2. In other embodiments, the antimicrobial solution is another suitable antimicrobial solution (e.g., including other formulations, etc.), as discussed above.

At optional initial step 202, a solvent and a pH buffer system are combined (e.g., added, mixed, stirred, etc.). In some embodiments of the antimicrobial solution, no pH buffer is used.

At step 204, a solvent (with or without the pH buffer system combined) and a surfactant are combined, according to an exemplary embodiment. In an exemplary embodiment, the solvent and the surfactant are combined (e.g., added, mixed, stirred, etc.), and the surfactant is dispersed evenly in/with the solvent. According to an exemplary embodiment, the solvent is water and the surfactant is lauryl glucoside. In an exemplary embodiment, the water is included in the antimicrobial solution in the amount of from 89.5 to 98.2 wt. % based on the total weight of the antimicrobial solution (e.g., 84.08%, 89.86%, etc.), and/or the lauryl glucoside is included in the antimicrobial solution in the amount of from 0.05 to 2.5 wt. % based on the total weight of the antimicrobial solution. In some embodiments, the surfactant (e.g., the lauryl glucoside, etc.) is included in the antimicrobial solution in another amount wt. % based on the total weight of the antimicrobial solution (e.g., 4.0%, etc.).

In some embodiments, step 204 further includes separately heating the water and lauryl glucoside to approximately 35-40 degrees Celsius, and then adding the heated lauryl glucoside to the heated water.

At optional step 206, a pH adjuster may be added to the solvent and the surfactant, according to an exemplary embodiment. Adding a pH adjuster in option step 206 may be in place of mixing a pH buffer system in optional step 202. In an exemplary embodiment, after the solvent and the surfactant are combined (e.g., mixed at step 204, etc.), and the surfactant is dispersed evenly in/with the solvent, the pH adjuster is added to (e.g., combined with, mixed, stirred, etc.) the solvent and the surfactant. According to an exemplary embodiment, the pH adjuster is gluconodelta lactone. In an exemplary embodiment, the gluconodelta lactone is included in the antimicrobial solution in the amount of from 0 to 3.0 wt. % based on the total weight of the antimicrobial solution (e.g., 0.10%, etc.). Where the water and lauryl glucoside are warmed, the combination is removed from heat before adding the gluconodelta lactone, or removed from heat after the gluconodelta lactone is added. The combination may then continue mixing until it is at 30 degrees Celsius or less before continuing to step 208.

At step 208, an enhancing ingredient is added to the solvent, surfactant, and pH adjuster (if present), according to an exemplary embodiment. In an exemplary embodiment, after the solvent, the surfactant, and the pH adjuster (if present) are combined (e.g., mixed at step 206), the enhancing ingredient is added to (e.g., combined with, mixed, stirred, etc.) the solvent, surfactant, and pH adjuster. According to an exemplary embodiment, the enhancing ingredient is benzyl alcohol. In an exemplary embodiment, the benzyl alcohol is included in the antimicrobial solution in the amount of from 0.05 to 3.0 wt. % based on the total weight of the antimicrobial solution (e.g., 2.0%, etc.). In other embodiments, the enhancing ingredient is not benzyl alcohol; rather, the enhancing ingredient is any aromatic alcohol, preservative, or any other suitable enhancing ingredient.

At step 210, an antimicrobial agent is added to the solvent, surfactant, pH adjuster (if present), and enhancing ingredient, according to an exemplary embodiment. In an exemplary embodiment, after the solvent, surfactant, pH adjuster, and enhancing ingredient are combined (e.g., mixed at step 208), the antimicrobial agent is added to (e.g., combined with, mixed, stirred, etc.) the solvent, surfactant, pH adjuster, and enhancing ingredient. According to an exemplary embodiment, the antimicrobial agent is chlorhexidine gluconate. In an exemplary embodiment, the chlorhexidine gluconate is included in the antimicrobial solution in the amount of from 0.5 to 4.0 wt. % based on the total weight of the antimicrobial solution (e.g., 2.0%, etc.). In other embodiments, the chlorhexidine gluconate is included in the antimicrobial solution in another amount wt. % based on the total weight of the antimicrobial solution (e.g., 9.82%, etc.). In yet other embodiments, the antimicrobial agent is not chlorhexidine gluconate; rather, the antimicrobial agent is 1,6-bis(4-chloro-phenylbiguanide) hexane, cationic antimicrobial agent (or just antimicrobial), biguanide, bis-biguanide, or any other suitable antimicrobial agent.

In some embodiments, following step 210 a pH level of the antimicrobial solution (e.g., of steps 202-208) is obtained. In yet other embodiments, a plurality of PH levels of the antimicrobial solution (e.g., of steps 202-208) is obtained (e.g., at a first time, at a second time, at a third time, etc.). A pH buffer may be added to adjust the pH.

Figure 3:
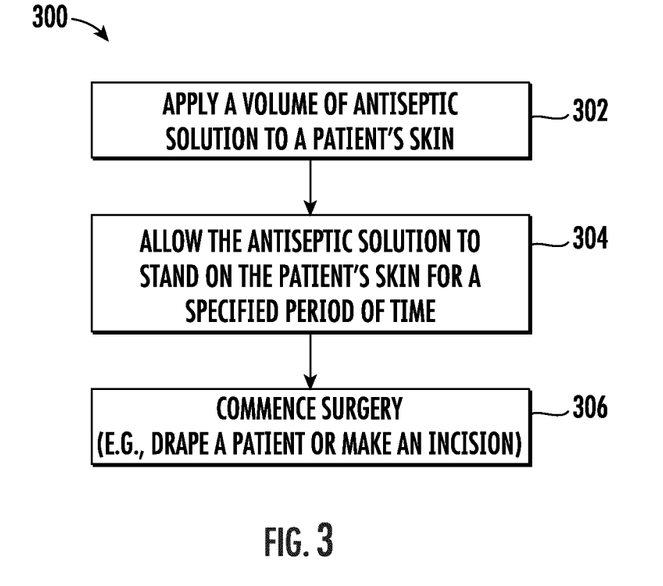
FIG. 3 is a block diagram of a method for preparation of a patient's skin for surgery, according to an exemplary embodiment.

Referring now to FIG. 3, an illustrative example of a method 300 for preparing a patient's skin for surgery is shown. Prior to the steps of method 300, a patient may be prepared for surgery and wheeled into an operating room. At step 302, a volume of an antiseptic solution as described herein is applied to a skin surface of the patient, in an amount effective to reduce bacteria on the skin surface. In some embodiments, the volume of solution applied is greater than or equal to 3 mL. More specifically, the volume may be 3 mL, 10 mL, 26 mL, or any other effective amount depending on the surface area to be prepared. In some embodiments, the patient may be draped (i.e., the procedure of covering a patient and surrounding areas with a sterile barrier to create and maintain a sterile field during a surgical procedure) prior to applying the antiseptic solution to the skin surface.

At step 304, the antiseptic solution is allowed to stand on the patient's skin for a period of time. According to an exemplary embodiment, the period of time is less than three minutes. The amount of time during which the solution stands on the skin is typically referred to as the "dry time." As used herein, "dry time" refers to the amount of time that the solution sits on a patient's skin after application, and does not mean that the solution is completely dry to the touch following the specified period of time.

At step 306, following the period of time (i.e., less than three minutes), surgery is commenced. As used herein, "commencing surgery" may include draping the patient (if not performed previously), or activation of a surgical tool, including cutting into the skin surface with a surgical device. In an exemplary embodiment, the surgical tool comprises a potential fire ignition source. Such surgical tools include, but are not limited to, electrosurgical equipment, electrocautery equipment, laser, and any other surgical tool which has the potential to generate an amount of heat sufficient to generate a flame.

As discussed above, according to exemplary embodiments herein, the antiseptic solution is non-flammable. This allows for a "dry time" (e.g., the time the solution is required to stand on the skin prior to commencing surgery) of less than three minutes. This is in contrast to antiseptic solutions currently used for surgical preparation that include components (such as at least 60% isopropyl or at least 60% ethyl alcohol), which, due to their flammability, require a dry time of more than three minutes before commencing surgery.

Although the Figures and description may illustrate a specific order of method steps, the order of such steps may differ from what is depicted and described, unless specified differently above. Also, two or more steps may be performed concurrently or with partial concurrence, unless specified differently above.

Figure 4:
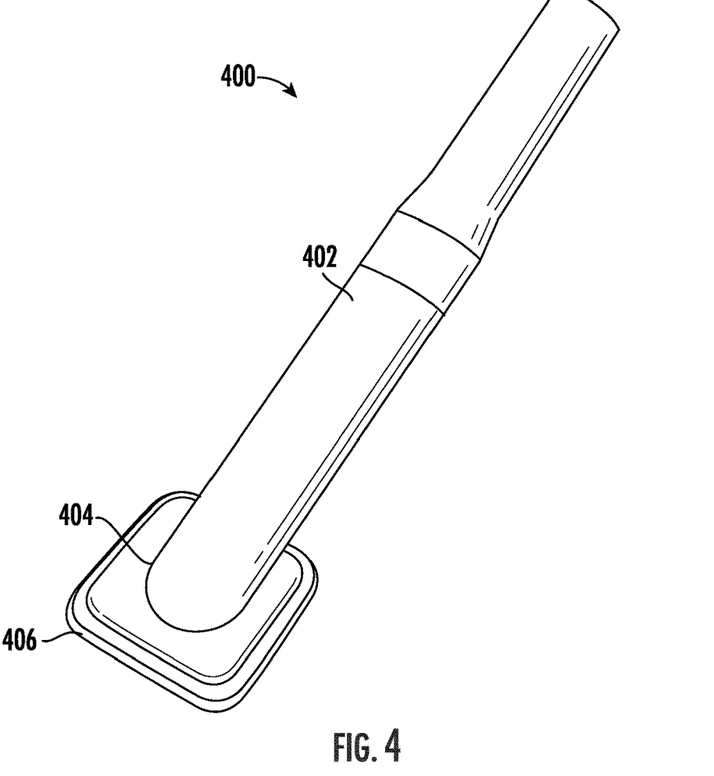
FIG. 4 is a top view of an application device, according to an exemplary embodiment.

Referring now to FIG. 4, an application device is shown according to an exemplary embodiment. In an exemplary embodiment, the application device is an applicator (e.g., shown as applicator 400), having a handle 402, a base 404, and a pad 406. The handle 402 may be an elongated hollow structure, configured as/to house a fluid reservoir (e.g., an ampoule, a capsule, a vial, etc.). In this regard, the handle 402 may be configured to receive, carry, and/or house a solution, and selectively move the solution from the handle 402 to other components of the applicator 400 (e.g., the base 404, the pad 406, etc.). The base 404 may be coupled to the handle 402 on a first side, and the pad 406 on a second side. According to an exemplary embodiment, the base 404 and the handle 402 are a uniform body; however, in other embodiments the base 404 and the handle 402 are separate components. Similar to the handle 402, the base may be configured as/to house a fluid reservoir (e.g., an ampoule, a capsule, a vial, etc.), and/or be configured to receive a solution from the handle 402 and subsequently (or simultaneously) provide the solution to the pad 406. The pad 406 may be coupled to the second side of the base 404, and be configured to receive a solution from the base 404 (or the handle 402) and provide (e.g., apply, etc.) the solution to a surface (e.g., the skin, a mucous membrane, etc.). In an exemplary embodiment, the pad 406 may be formed from foam (e.g., a polymer foam such as polyurethane foam, an open or close-celled foam, etc.), non-woven material, cloth, sponge, or any other suitable absorbent material. In this regard, the pad 106 may receive a solution, absorb the solution, and/or selectively provide the solution to a surface.

As discussed above, in some embodiments, the handle 402 and/or the base 404 are configured to house a fluid reservoir (e.g., an ampoule, a capsule, a vial, etc.). According to an exemplary embodiment, the fluid reservoir is an ampoule containing a solution. The ampoule may be formed as a uniform structure, or may include a cover (e.g., a plastic or foil cover, etc.), and may be formed of any suitable material (e.g., glass, polyethylene, polypropylene, polyolefin, other suitable plastics, etc.). According to an exemplary embodiment, the applicator 104000 may be manipulated in order to modify the ampoule and release the solution inside. For example, a button may be pressed, pressure can be applied to the handle 402, the base 404, and/or the pad 406 (e.g., moved, pressed, etc.), the handle 402 may be rotated, etc., which may break the top of the ampoule, puncture the cover of the ampoule, puncture the body of the ampoule, crush the entire ampoule, or otherwise modify the ampoule to release the solution. According to an exemplary embodiment, once the solution is released from the ampoule, the solution can be selectively moved from the handle 402 and/or the base 404, to the pad 406. The pad 406 may receive and/or absorb the solution, and may be used to selectively provide (e.g., apply, etc.) the solution to a surface.

Also discussed above, in other embodiments the handle 402 and/or the base 404 are configured as a fluid reservoir containing a solution. In an exemplary embodiment, the handle 402 and/or the base 404 may be manipulated to selectively move the solution from the handle 402 and/or the base 404 to the pad 406. For example, a button may be pressed, pressure may be applied to the handle 402, the base 404, and/or the pad 406 (e.g., pinched, squeezed, pressed downward on a surface, etc.), etc., which may selectively move the solution from the handle 402 and/or the base 404 to the pad 406. As discussed above, the pad 406 may receive and/or absorb the solution, and may be used to selectively provide (e.g., apply, etc.) the solution to a surface.

Figure 5:
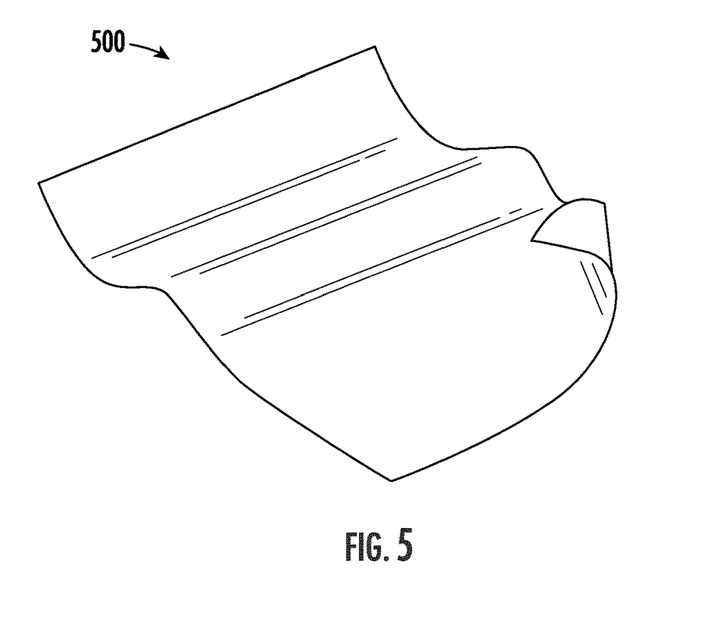
FIG. 5 is a top view of another application device, according to an exemplary embodiment.

Referring now to FIG. 5, an application device is shown according to an exemplary embodiment. In an exemplary embodiment, the application device is a cloth (e.g., shown as cloth 200). The cloth 500 may be woven, knitted, non-woven, velour, felt, flocked, needle-punched, or any other suitable composition and/or a combination thereof. The cloth 500 may also be formed of cotton, polyester, wool, or any other suitable absorbent material, and may be any suitable shape (e.g., square, rectangular, circular, etc.). Similar to the pad 406 of FIG. 4, the cloth 500 may be configured to receive a solution (e.g., the antimicrobial solution), carry the solution, absorb the solution, and/or selectively provide (e.g., apply, etc.) the solution to a surface (e.g., the skin, a mucous membrane, etc.).

According to an exemplary embodiment, the applicator 400 and/or the cloth 500 is configured to receive a solution and selectively apply the solution to a surface (e.g., the skin). According to an exemplary embodiment, the solution is an antimicrobial solution. The antimicrobial solution may comprise one or more antimicrobial agents and/or solvents. In this regard, when the antimicrobial solution is applied to particular surfaces (e.g., skin, mucous membranes, etc.) the antimicrobial solution is capable of killing or inhibiting bacterial growth. As such, the antimicrobial solution may be suitable for disinfecting surfaces, for example the skin or mucous membranes of a patient prior to a surgical operation.

All or some of the components described herein may be provided in a kit, which may be a pre-packaged arrangement. For example, the applicator 100 and/or the cloth 200 may be provided with an antimicrobial solution (e.g., the antimicrobial solution described in Tables 1 and 2, any other solution described herein, etc.) in a pre-packaged antimicrobial assembly, with the antimicrobial solution inside the applicator 400 and/or the cloth 500, and/or the antimicrobial solution impregnated in the applicator 400 and/or the cloth 500. In this regard, the antimicrobial assembly may be pre-packaged, and may be un-packaged to provide the antimicrobial solution to a surface (e.g., skin, a mucous membrane, etc.). In some embodiments, a fluid reservoir (e.g., an ampoule, a vial, a container, etc.) is provided with an antimicrobial solution (e.g., the antimicrobial solution described in Table 1, etc.) in a pre-packaged assembly. In this regard, the fluid reservoir may be pre-packaged, and may be un-packaged to be combined with an applicator (e.g., the applicator 400, the cloth 500, etc.). In an exemplary embodiment, the applicator, the fluid reservoir, and/or the antimicrobial solution are packaged together by wrapping with a packaging material to form a package; however, in other embodiments other packaging arrangements may be utilized.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

As used herein, the singular forms "a," "an," and "the" designate both the singular and the plural, unless expressly stated to designate the singular only.

As utilized herein with respect to numerical ranges, the terms "approximately," "about," "substantially," and similar terms generally mean+/−10% of the disclosed values, unless specified otherwise. It is also to be understood that any ranges and subranges disclosed herein describe and contemplate all ranges, subranges, and individual values embraced thereby, including whole and/or fractional values, even if such values are not expressly written herein. For example, such ranges and subranges may be further delineated into relevant halves, thirds, quarters, fifths, and so on. As just one example, a range "of from 0.5 to 4.0" may be further delineated into a lower third, i.e. from 0.5 to 1.66, a middle third, i.e. from 1.66 to 2.83, and an upper third, i.e. from 2.83 to 4.0, as well as each individual value from 0.5 to 4.0 inclusive, which individually and collectively are within the scope of this disclosure to the same extent as if expressly set forth herein. For example, a range "of from 0.5 to 4.0" includes a disclosure of all integers within that range, such as 3, as well as all non-integer values within that range, such as 3.1, to the same extent as if expressly set forth herein.

As used herein "patient" denotes any animal undergoing surgery as discussed herein, including humans and non-human mammals.

Several embodiments have been discussed in the foregoing description. However, the embodiments discussed herein are not intended to be exhaustive or limit the invention to any particular form.

What is claimed is:

1. A method for the preparation of a patient's skin prior to surgery, comprising:
    applying a volume of a non-flammable antiseptic solution to the skin surface prior to surgery in an amount effective at reducing bacteria on the skin surface; and
    allowing the non-flammable antiseptic solution to stand on the skin surface for about 1 second to about three minutes before commencing surgery,
    wherein the non-flammable antiseptic solution comprises about 0.5% wt to about 4.0% wt of chlorhexidine gluconate and about 0.5% wt to about 3% wt of benzyl alcohol, and is at least as effective at reducing bacteria as a flammable antiseptic solution comprising 70% wt of isopropyl alcohol or 70% wt of isopropyl alcohol and 2% wt of chlorhexidine gluconate, and
    wherein the volume of the non-flammable antiseptic solution is dependent on the surface area to be prepared.

2. The method of claim 1, wherein the non-flammable antiseptic solution comprises 2% wt of the benzyl alcohol 2% wt of the chlorhexidine gluconate.

3. The method of claim 2, wherein the non-flammable antiseptic solution consists essentially of the 2% wt of chlorhexidine gluconate, the 2% wt of benzyl alcohol, and 96% wt of water.

4. The method of claim 1, wherein the non-flammable antiseptic solution further comprises a surfactant.

5. The method of claim 4, wherein the surfactant is lauryl glucoside.

6. The method of claim 1, wherein commencing surgery comprises activating a surgical tool comprising a potential fire ignition source.

7. The method of claim 6, wherein the potential fire ignition source is one or more selected from electrosurgical equipment, electrocautery equipment, and a laser.

8. The method of claim 1, wherein commencing surgery comprises draping the patient.

9. The method of claim 1, wherein the volume of the non-flammable antiseptic solution applied to the skin surface is greater than or equal to 3 mL.

10. The method of claim 9, wherein the volume of the non-flammable antiseptic solution applied to the skin surface is selected from 3 mL, 10 mL, and 26 mL.

11. The method of claim 1, wherein the bacteria has the potential to cause a skin infection.

12. The method of claim 1, wherein the non-flammable antiseptic solution achieves a log reduction of bacteria that is greater than or equal to $X-0.5 \log^{10}$, wherein X is the log reduction achieved by the flammable antiseptic solution comprising 70% wt of isopropyl alcohol or 70% wt of isopropyl alcohol and 2% wt of chlorhexidine gluconate.

13. The method of claim 1, wherein the bacteria is gram positive.

14. The method of claim 1, wherein the bacteria is selected from one or more of *Enterococcus faecalis, Enterococcus faecium, Staphylococcus aureus, Burkholderia cepacian, Acinetobacter baumannii, Bacteroides fragilis, Proteus mirabilis, Serratia marcescens*, or *Staphylococcus haemolyticus*.

15. The method of claim 1, wherein the bacteria is gram negative.

16. A method for the preparation of a patient's skin prior to surgery, comprising:
    applying a volume of a non-flammable antiseptic solution to the skin surface prior to surgery in an amount effective at reducing bacteria on the skin surface;
    wherein the non-flammable antiseptic solution comprises about 0.5% wt to about 4.0% wt of chlorhexidine gluconate and about 0.5% wt to about 3% wt of benzyl alcohol, and achieves a log reduction of bacteria that is greater than or equal to $X-0.5 \log^{10}$,
    wherein X is the log reduction achieved by a flammable antiseptic solution comprising 70% wt of isopropyl alcohol or 70% wt of isopropyl alcohol and 2% wt of chlorhexidine gluconate, and
    wherein the volume of the non-flammable antiseptic solution is dependent on the surface area to be prepared.

17. The method of claim 16, wherein the non-flammable antiseptic solution comprises 2% wt of the benzyl alcohol and 2% wt of the chlorhexidine gluconate.

18. The method of claim 16, wherein the volume of the non-flammable antiseptic solution applied to the skin surface is greater than or equal to 3 mL.

19. The method of claim 16, further comprising allowing the non-flammable antiseptic solution to dry for less than three minutes before activating a potential fire ignition source.

20. The method of claim 19, wherein the potential fire ignition source is one or more selected from electrosurgical equipment, electrocautery equipment, and a laser.

\* \* \* \* \*